United States Patent
Hanazono et al.

(10) Patent No.: US 8,522,428 B2
(45) Date of Patent: Sep. 3, 2013

(54) METHOD FOR PRODUCING A SENSOR BOARD

(75) Inventors: Hiroyuki Hanazono, Osaka (JP); Hiroshi Yamazaki, Osaka (JP)

(73) Assignee: Nitto Denko Corporation, Osaka (JP)

( * ) Notice: Subject to any disclaimer, the term of this patent is extended or adjusted under 35 U.S.C. 154(b) by 984 days.

(21) Appl. No.: 12/461,492

(22) Filed: Aug. 13, 2009

(65) Prior Publication Data
US 2010/0073886 A1 Mar. 25, 2010

(30) Foreign Application Priority Data
Sep. 19, 2008 (JP) ................................ 2008-241425

(51) Int. Cl.
*H05K 3/02* (2006.01)
*H05K 3/10* (2006.01)
(52) U.S. Cl.
USPC .............................. 29/846; 29/830; 427/126.3
(58) Field of Classification Search
USPC .................. 422/50, 68.1, 98; 427/79, 126.2, 427/126.3; 29/830, 846, 851
See application file for complete search history.

(56) References Cited

U.S. PATENT DOCUMENTS

| | | | |
|---|---|---|---|
| 5,571,401 A | 11/1996 | Lewis et al. | |
| 5,698,089 A | 12/1997 | Lewis et al. | |
| 5,725,957 A * | 3/1998 | Varaprasad et al. | 427/126.3 |
| 5,920,455 A * | 7/1999 | Shah et al. | 427/79 |
| 2003/0134089 A1 | 7/2003 | Schultz et al. | |
| 2010/0072065 A1 | 3/2010 | Naito et al. | |

FOREIGN PATENT DOCUMENTS

| | | |
|---|---|---|
| JP | 337559 A | 2/1991 |
| JP | 11-503231 | 3/1999 |
| JP | 2000-097894 | 4/2000 |
| JP | 2007-090251 | 4/2007 |
| JP | 2009-543060 | 12/2009 |
| WO | WO-2008-002837 A2 | 1/2008 |
| WO | WO2008/084582 A1 | 7/2008 |

OTHER PUBLICATIONS

K. Steirer et al. "Ultrasonically sprayed and inkjet printed thin film electrodes for organic solar cells" Thin Solid Films vol. 517, Nov. 11, 2008, pp. 2781-2786.
L. Castaneda, Effects of palladium coatings on oxygen sensors of titanium dioxide thin films, Materials Science and Engineering, 2007 vol. 139, pp. 149-154.
Mayu Hashimoto et al., Preparation of porous ceramic powders by pyrolysis of atmozied precursor solutions . . . , Chemical Sensors, 2007, vol. 23 Supplement A, pp. 115-117.
A.V. Tadeev et al., Sensor properties of Pt doped Sn02 thin films for detecting CO, Thin Solid Films, 1999, vol. 337, pp. 163-165.

* cited by examiner

*Primary Examiner* — Donghai D. Nguyen
(74) *Attorney, Agent, or Firm* — Jean C. Edwards, Esq.; Edwards Neils PLLC

(57) ABSTRACT

A method for producing a sensor board includes the steps of preparing an insulating layer; forming at least a pair of electrodes on the insulating layer; and forming a conductive layer by spraying a conductive component-containing liquid onto the insulating layer by an ultrasonic spray method so as to cover the electrodes.

5 Claims, 3 Drawing Sheets

(a)

(b)

(c)

(d)

METHOD FOR PRODUCING A SENSOR BOARD

CROSS REFERENCE TO RELATED APPLICATION

The present application claims priority from Japanese Patent Application No. 2008-241425 filed on Sep. 19, 2008, the content of which is hereby incorporated by reference in its entirety.

BACKGROUND OF THE INVENTION

1. Field of the Invention

The present invention relates to a method for producing a sensor board, and a sensor board obtained by the producing method. More particularly, the present invention relates to a method for producing a sensor board for mainly detecting the type and the amount of gas, and a sensor board obtained by the producing method.

2. Description of Related Art

Substance sensors for detecting gas or fluid are conventionally used in various industrial applications. Such substance sensors are used for qualitative or quantitative analysis of a specific gas or fluid.

For example, it has been proposed that a plurality of sensor arrays are provided which includes a register containing a conductive substance, and a first and a second conductive leads arranged at a spaced interval to each other so as to be electrically connected through the register (cf. Japanese Unexamined Patent Publication No. 11-503231).

SUMMARY OF THE INVENTION

In Japanese Unexamined Patent Publication No. 11-503231, the registers are formed by applying a solution containing a conductive substance corresponding to the register in each sensor array and a solvent which dissolves the conductive substance, to the first and the second conductive leads so that the registers are in contact with these conductive leads, and then drying the applied solution (solution casting). Alternatively, the solution is known to be applied by an air spray method.

However, when the above-mentioned solution is merely applied onto the first and the second conductive leads or applied by the air spray method, the solution wet-spreads during the time from the application of the solution to the drying thereof. Therefore, when the solvent in the solution evaporates, the conductive substance contained in the solution agglomerates and/or is unevenly distributed, thereby making the thickness or the spreading of the register thus formed uneven in some cases. As a result, the register formed by the above-mentioned method may not accurately detect a substance. Further, the above-mentioned method may cause excessive application or scattering of the solution, resulting in the loss of materials.

It is an object of the present invention to provide a method for producing a sensor board capable of detecting a substance with high accuracy by forming a conductive layer with a uniform thickness, and a sensor board obtained by the producing method.

The method for producing a sensor board according to the present invention includes the steps of preparing an insulating layer; forming at least a pair of electrodes on the insulating layer; and forming a conductive layer by spraying a conductive component-containing liquid onto the insulating layer by an ultrasonic spray method so as to cover the electrodes.

In the method for producing a sensor board according to the present invention, it is preferable that the conductive component-containing liquid contains an organic solvent, a conductive particle, and a non-conductive substance.

In the method for producing a sensor board according to the present invention, it is preferable that the conductive component-containing liquid has a viscosity at 25° C. of 0.05 Pa·s or less.

The present invention includes the sensor board obtained by the method for producing a sensor board as described above.

According to the method for producing the sensor board of the present invention, a conductive layer can be uniformly formed.

Further, according to the method for producing the sensor board of the present invention, there is little loss of the conductive component-containing liquid, thereby achieving a reduction of production cost of the sensor board.

Further, the sensor board obtained by the producing method can detect a substance with reliability and high accuracy.

DETAILED DESCRIPTION OF PREFERRED EMBODIMENTS

Figure 1:
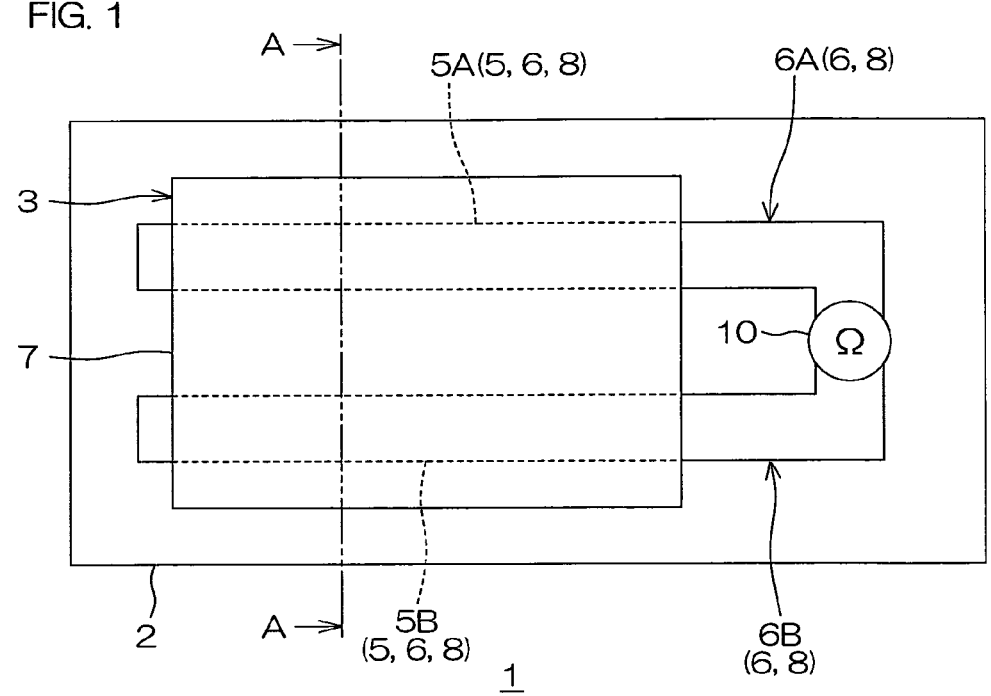
FIG. 1 is a plan view illustrating a sensor board of an embodiment obtained by a method for producing a sensor board according to the present invention.
Figure 2:
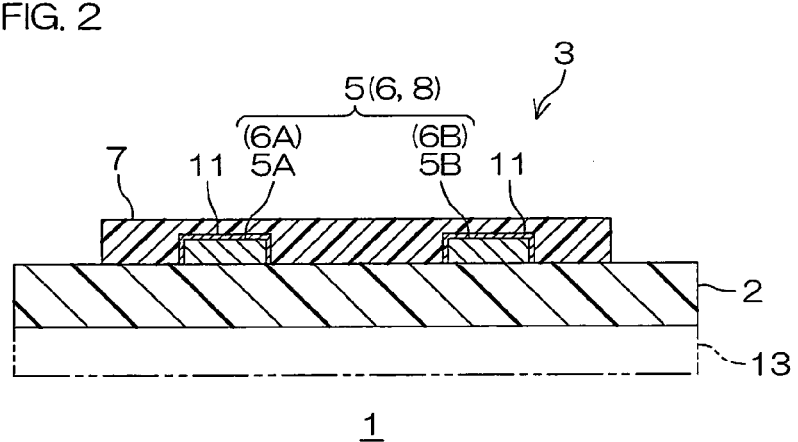
FIG. 2 is a sectional view taken along the line A-A in FIG. 1.
Figure 3:
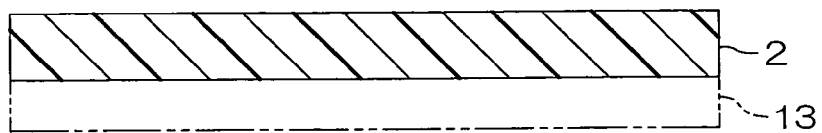
FIG. 3 is a process diagram showing a method for producing the sensor board shown in FIG. 1,
(a) showing the step of preparing an insulating base layer,
(b) showing the step of forming a conductive pattern,
(c) showing the step of forming a protective layer, and
(d) showing the step of forming a conductive layer.
Figure 3:
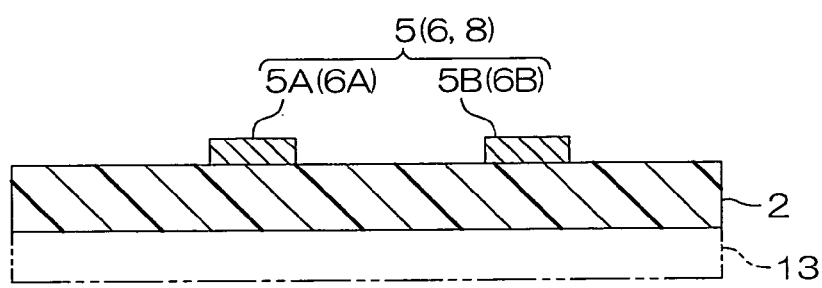
Figure 3:
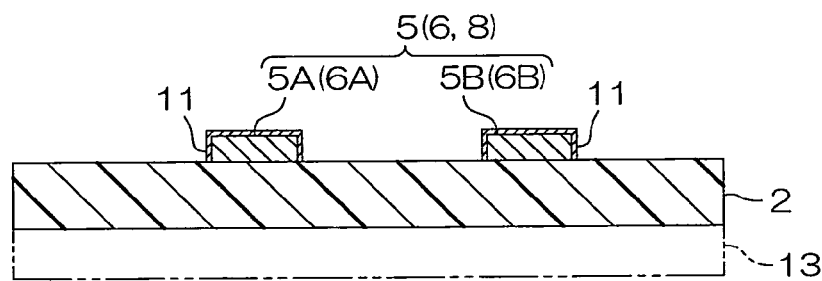
Figure 3:
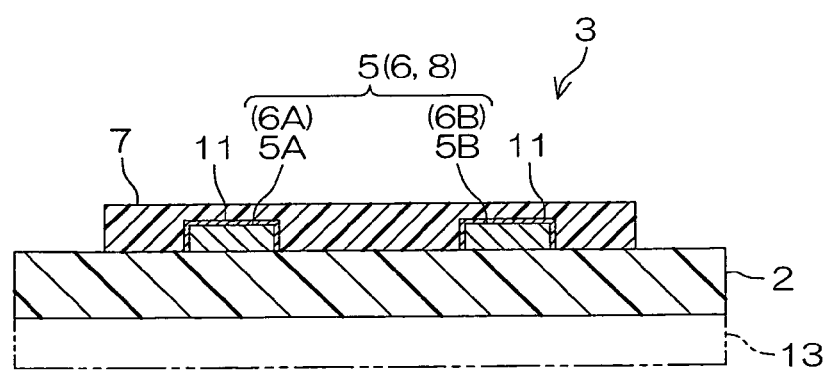

FIG. 1 is a plan view illustrating a sensor board of an embodiment obtained by a method for producing a sensor board according to the present invention, FIG. 2 is a sectional view taken along the line A-A in FIG. 1; and FIG. 3 is a process diagram showing a method for producing the sensor board shown in FIG. 1. To clarify the relative position of a conductive pattern, a protective layer 11 is omitted in FIG. 1.

In FIG. 1, the sensor board 1 includes an insulating base layer 2 as an insulating layer and a conductive pattern 8 formed on the insulating base layer 2.

The insulating base layer 2 is formed from, for example, a rectangular sheet extending in the lengthwise direction.

The conductive pattern 8 is formed in the form of a wired circuit pattern including a pair of wires 6 on a surface of the insulating base layer 2.

The pair of wires 6 is opposed at a spaced interval to each other in a direction perpendicular to the lengthwise direction (hereinafter referred to as the widthwise direction), and is formed so as to extend in the lengthwise direction.

Specifically, the pair of wires 6 includes a first wire 6A arranged at one side in the widthwise direction, and a second wire 6B arranged at the other side in the widthwise direction. One lengthwise end portions of the wires 6 are bent into the inner side in the opposed direction and are connected with an electrical resistance detector 10.

As shown in FIG. 2, a protective layer 11 which covers the conductive pattern 8 is formed on the conductive pattern 8.

The protective layer 11 is directly formed on the surfaces (the upper surface and the side surfaces) of the first wire 6A and the second wire 6B.

The sensor board 1 thus formed includes a detection portion 3.

The detection portion 3 is a region for detecting a substance on the sensor board 1 and is divided into a generally rectangular shape in plane view on the insulating base layer 2 as shown in FIG. 1. The detection portion 3 includes a pair of (two) electrodes 5 and a conductive layer 7.

Namely, the pair of electrodes 5 is portions of the wires 6 included in the region of the detection portion 3. Of the pair of electrodes 5, one electrode 5 corresponding to the first wire 6A is defined as a first electrode 5A, and the other electrode 5 corresponding to the second wire 6B as a second electrode 5B.

The conductive layer 7 is formed on the insulating base layer 2 in a generally rectangular shape in plane view so as to cover the pair of electrodes 5 and defines the outer shape of the detection portion 3.

More specifically, the conductive layer 7 is formed on the upper surface of the insulating base layer 2 so as to be in contact with the surface of the protective layer 11 and the upper surface of the insulating base layer 2 exposed from the protective layer 11. Thus, the conductive layer 7 is electrically connected with the first electrode 5A and the second electrode 5B so as to span between the first electrode 5A and the second electrode 5B.

Next, a method for producing the sensor board 1 is described with reference to FIG. 3.

In this method, as shown in FIG. 3(a), an insulating base layer 2 is first prepared.

As an insulating material for forming the insulating base layer 2, for example, synthetic resin such as a liquid crystal polymer (LCP; a polymer of an aromatic or aliphatic dihydroxy compound, a polymer of an aromatic or aliphatic dicarboxylic acid, a polymer of an aromatic hydroxycarboxylic acid, a polymer of an aromatic diamine, an aromatic hydroxyamine, or an aromatic aminocarboxylic acid, etc.), polyethylene terephthalate (PET), polyimide (PI), polyether nitrile, polyether sulfone, polyethylene naphthalate, polyphenyline sulfide (PPS), polyether imide (PEI), and polyvinyl chloride is used. These insulating materials can be used alone or in combination.

As such insulating material, a material having a low coefficient of water absorption, humidity expansion, thermal expansion, and gas permeability is preferably used.

Among them, a liquid crystal polymer or polyethylene terephthalate is preferably used. Since a liquid crystal polymer or polyethylene terephthalate has a low coefficient of water absorption or gas permeability (oxygen permeability, etc.), the insulating base layer 2 can be prevented from swelling due to absorption of water vapor in the ambient air, and the conductive layer 7 can be prevented from being affected due to penetrating of gas or water vapor from the undersurface of the insulating base layer 2. Therefore, a detection error based on the swelling of the insulating base layer 2 and a detection error based on the insulating base layer 2 affected by the penetration can be prevented.

To prepare the insulating base layer 2, for example, a sheet of the above-mentioned insulating material is prepared. Alternatively, the insulating base layer 2 can be prepared by forming a film of a varnish of an insulating material on a stripping plate, which is not shown, by casting, drying the film, and then curing the dried film as required.

Commercially available products can be used as the sheet of the above-mentioned insulating material, and, examples thereof include a VECSTAR series sheet (a liquid crystal polymer sheet, manufactured by Kuraray Co., Ltd.), a BIAC series sheet (a liquid crystal polymer sheet, manufactured by JAPAN GORE-TEX INC.), and a Lumirror series sheet (a polyethylene terephthalate sheet, manufactured by Toray Industries, Inc.).

The insulating base layer 2 thus formed has a thickness in the range of, for example, 5 to 30 μm, or preferably 5 to 25 μm.

Subsequently, in this method, as shown in FIG. 3(b), a conductive pattern 8 is formed on the insulating base layer 2.

As a material for forming the conductive pattern 8, for example, a conductive material such as copper, nickel, gold, tin, rhodium, solder, or alloys thereof is used. Among them, copper is preferably used from the viewpoint of conductivity and processability.

The conductive pattern 8 is formed in the form of the above-mentioned wired circuit pattern by a known patterning method such as a printing method, an additive method, or a subtractive method.

In the printing method, for example, a paste containing microparticles of the above-mentioned material is screen-printed on a surface of the insulating base layer 2 in the above-mentioned pattern and then sintered. This directly forms the conductive pattern 8 on the surface of the insulating base layer 2.

In the additive method, for example, a thin conductive film (a seed layer), which is not shown, is first formed on a surface of the insulating base layer 2. The thin conductive film is formed by sequentially laminating a thin chromium film and a thin copper film by sputtering, or preferably chromium sputtering and copper sputtering.

A plating resist is then formed in a pattern reverse to the above-mentioned conductive pattern on a surface of the thin conductive film, and the conductive pattern 8 is formed on the surface of the thin conductive film exposed from the plating resist by electrolytic plating. Thereafter, the plating resist and the thin conductive film on which the plating resist is laminated are removed.

In the subtractive method, for example, a two-layer substrate (copper foil two-layer substrate, etc.) on which a conductive layer made of the above-mentioned conductive material is preliminarily laminated is first prepared on a surface of the insulating base layer 2, and a dry film resist is laminated on the conductive layer. Thereafter, the dry film resist is exposed to light and developed. Then, an etching resist having the same pattern as the above-mentioned conductive pattern 8 is formed. Subsequently, the conductive layer exposed from the etching resist is subjected to chemical etching (wet etching), and the etching resist is then removed to form the conductive pattern 8. To prepare the two-layer substrate, a known adhesive layer can be interposed between the insulating base layer 2 and the conductive layer as required.

In the formation of the conductive pattern 8 by the above-mentioned subtractive method, commercially available products can be used as the copper foil two-layer substrate, and, for example, a liquid crystal polymer copper-clad laminate (ESPANEX L series, single-sided, standard type/P type, manufactured by Nippon Steel Chemical Co., Ltd.) in which a conductive layer made of copper is preliminarily laminated on a surface of the insulating base layer 2 made of liquid crystal polymer is used.

Among these patterning methods, a printing method is preferably used. This method ensures that the conductive pattern 8 can be directly formed on the surface of the insulating base layer 2, so that a specific gas can be detected with high accuracy.

The conductive pattern 8 thus formed has a thickness in the range of, for example, 5 to 30 µm, or preferably 5 to 20 µm. The length (length in lengthwise direction) of the respective wires 6 may be the same or different from each other, and is in the range of, for example, 5 to 100 mm, or preferably 5 to 50 mm. Each of the wires 6 (electrodes 5) has a width (length in widthwise direction) in the range of, for example, 10 to 500 µm, or preferably 20 to 300 µm. A spacing between the wires 6 (electrodes 5) is in the range of, for example, 0.1 to 10 mm, or preferably 0.2 to 4 mm.

A pair of electrodes 5 is simultaneously formed by forming the conductive pattern 8.

Subsequently, in this method, as shown in FIG. 3(*c*), a protective layer 11 is formed so as to cover the conductive pattern 8.

As a material for forming the protective layer 11, a metal material such as gold is used. When the protective layer 11 is formed as a gold layer, even if the specific gas to be detected is acid gas, the gold layer can reliably prevent corrosion of the conductive pattern 8.

The protective layer 11 is formed by a known thin film forming method such as sputtering and plating such as electroless plating or electrolytic plating, so as to cover the conductive pattern 8.

The protective layer 11 thus formed has a thickness in the range of, for example, 0.05 to 3 µm, or preferably 0.5 to 1.5 µm.

Subsequently, in this method, as shown in FIG. 3(*d*), a conductive layer 7 is formed on the insulating base layer 2 in a generally rectangular shape in plane view so as to cover the protective layer 11.

The conductive layer 7 is formed from a conductive material which is formed from, for example, a mixture of a conductive particle exhibiting conductivity and a non-conductive substance which swells according to the type or the amount (concentration) of a specific gas.

The conductive particle that may be used includes, for example, an organic conductor, an inorganic conductor, or a mixed organic/inorganic conductor.

Examples of the organic conductor include conductive polymers such as polyaniline, polythiophene, polypyrrole, and polyacetylene; carbonaceous materials such as carbon blacks, graphite, corks, and C60; and charge transfer complexes such as tetramethylparaphenylenediamine-chloranile, alkali metal tetracyanoquinolinodimethane complexes, and tetrathiofulvalene halide complexes.

Examples of the inorganic conductor include metals such as silver, gold, copper, and platinum; alloys of the above-mentioned metals such as Au—Cu alloys; highly doped semiconductors such as silicon, gallium arsenide (GaAs), indium phosphide (InP), molybdenum sulfide ($MoS_2$), and titanium oxide ($TiO_2$); conductive metal oxides such as indium oxide ($In_2O_3$), tin oxide ($SnO_2$), and sodium platinum oxide ($Na_xPt_3O_4$); and superconductors such as $YBa_2Cu_3O_7$ and $Tl_2Ba_2Ca_2Cu_3O_{10}$.

Examples of the mixed organic/inorganic conductor include tetracyano-platinate complexes, iridium-halocarbonyl complexes, and stacked macrocyclic complexes.

These conductive particles can be used alone or in combination.

The non-conductive substance that may be used includes, for example, non-conductive organic polymers such as main chain carbon polymers, main chain acyclic heteroatom polymers, and main chain heterocyclic polymers.

Examples of the main chain carbon polymer include polydiene, polyalkene, polyacrylic, polymethacrylic, polyvinyl ether, polyvinyl thioether, polyvinyl alcohol, polyvinyl ketone, polyvinyl halide, polyvinyl nitrile, polyvinyl ester, polystyrene, poly (α-methylstyrene), polyarylene, polyvinyl alcohol, and polyvinyl acetate.

Examples of the main chain acyclic heteroatom polymer include polyoxide, polycarbonate, polyester, polyanhydride, polyurethane, polysulfonate, polysiloxane, polysulfide, polythioester, polysulfone, polysulfone amide, polyamide, polyamide amine (polyamide amine dendrimer), polyurea, polyphosphazene, polysilane, and polysilazane.

Examples of the main chain heterocyclic polymer includes poly(furan tetracarboxylic acid diimides), polybenzoxazoles, polyoxadiazoles, polybenzothiadinophenothiazines, polybenzothiazoles, polypyrazinoquinoxalines, polypyromellitimides (polypiromenitimides), polyquinoxalines, polybenzimidazoles, polyoxindoles, polyoxoisoindolines, polydioxoisoindolines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyvinyl pyrrolidones, and polybisphenols, or other hydrocarbons.

As the non-conductive substance, for example, oligomers such as polyester acrylate oligomer may also be used.

These non-conductive substances can be used alone or in combination.

To form the conductive layer 7, a conductive component-containing liquid (solution and/or suspension) containing an organic solvent, a conductive particle, and a non-conductive substance (or precursors (monomers) thereof) is prepared and then sprayed onto the insulating base layer 2 by an ultrasonic spray method.

The organic solvent having a boiling point of 40 to 120° C. is preferable, and examples thereof include ketones such as acetone, methyl ethyl ketone, and methyl isobutyl ketone; alcohols such as methyl alcohol, ethyl alcohol, isopropyl alcohol, and n-propyl alcohol; aromatic hydrocarbons such as toluene and xylene; halogenated hydrocarbons such as a methylene chloride; ethers such as tetrahydrofuran (THF); and nitriles such as acetonitrile.

These organic solvents can be used alone or in combination.

In the case of preparing the conductive component-containing liquid as a solution, an organic solvent (solvent) capable of dissolving a conductive particle and a non-conductive substance (or precursors thereof) is selected as the organic solvent, and such organic solvent is mixed with the conductive particle and the non-conductive substance (or the precursors thereof) to be dissolved.

Alternatively, in the case of preparing the conductive component-containing liquid as a suspension, an organic solvent (dispersion medium) capable of dispersing a conductive particle is selected as the organic solvent, and the conductive particle is suspended in the organic solvent. In such case, for example, the conductive particle is suspended in the organic solvent with a known agitator such as a forced agitator or an ultrasonic agitator. In the preparation of the suspension, when two or more kinds of conductive particles are used, some of the conductive particles are suspended and the others can be dissolved therein.

As for the mixing proportions of the respective ingredients to prepare the conductive component-containing liquid, per 100 parts by weight of the non-conductive substance, the conductive particle is in the range of, for example, 10 to 50 parts by weight, or preferably 20 to 35 parts by weight, and the organic solvent is in the range of, for example, 2000 to 20000 parts by weight, or preferably 5000 to 15000 parts by weight.

If desired, known additives such as a catalyst can be added to the conductive component-containing liquid.

In the preparation of the conductive component-containing liquid, for example, when a precursor of the conductive particle is used, the precursor (monomer) is allowed to react (polymerize) together with spraying of the conductive component-containing liquid by an ultrasonic spray method and with evaporation of the organic solvent, to thereby produce a conductive particle. More specifically, for example, in the case of using pyrrole as a precursor, when the conductive component-containing liquid (solution) containing THF, pyrrole, and molybdophosphoric acid (catalyst) is sprayed and the THF is also evaporated, the pyrrole is oxidized and polymerized, to thereby produce polypyrrole.

The conductive component-containing liquid thus prepared has a viscosity at 25° C. in the range of, for example, 0.05 Pa·s or less, preferably $1 \times 10^{-4}$ to 0.05 Pa·s, or more preferably $5 \times 10^{-4}$ to 0.01 Pa·s.

The ultrasonic spray method is a spray coating method using an ultrasonic wave, for example, in which a liquid is sprayed in the form of a liquid droplet (in mist form) having a fine particle diameter by ultrasonic vibration. Thus, a coating solution can be applied to an object uniformly and effectively.

When the conductive component-containing liquid is sprayed onto the insulating base layer 2 by an ultrasonic spray method, it is sprayed in the form of a liquid droplet having a fine diameter. Therefore, the organic solvent in the conductive component-containing liquid evaporates by the time when the liquid droplet of the conductive component-containing liquid reaches the insulating base layer 2. Thus, such ultrasonic spray method can suppress wetting and spreading of the conductive component-containing liquid. As a result, agglomeration and/or uneven distribution of the conductive material (conductive particle and non-conductive substance) can be suppressed.

In the spraying of the conductive component-containing liquid by the ultrasonic spray method, the frequency of the ultrasonic wave is in the range of, for example, 20 to 150 kHz, or preferably 60 to 120 kHz. When the frequency of the ultrasonic wave is within the above-mentioned range, the sprayed conductive component-containing liquid can have an extremely finer diameter than the liquid droplet obtained by an air spray method.

More specifically, for example, the use of an ultrasonic wave having a frequency of 60 kHz can make the particle diameter of the conductive component-containing liquid about 35 μm or less while the use of an ultrasonic wave having a frequency of 120 kHz can make the particle diameter of the conductive component-containing liquid about 20 μm or less.

The finer diameter the liquid droplet of the conductive component-containing liquid has, the more uniformly the conductive component-containing liquid can be sprayed onto the insulating base layer 2, so that the thickness of the conductive layer 7 thus obtained can be made more uniform.

Commercially available ultrasonic spray devices can be used to spray the above-mentioned conductive component-containing liquid onto the insulating base layer 2 by the ultrasonic spray method. Examples of the ultrasonic spray device include an ultrasonic spray nozzle (manufactured by Sono-Tek Corporation).

To spray the conductive component-containing liquid onto the insulating base layer 2, more specifically, for example, an ultrasonic spray device is first installed so that its jet opening faces the insulating base layer 2, and the conductive component-containing liquid is then sprayed from the jet opening of the ultrasonic spray device onto the insulating base layer 2 that is, for example, 10 to 200 mm, or preferably 30 to 100 mm spaced apart from the jet opening thereof.

Such spraying allows the organic solvent in the conductive component-containing liquid to well evaporate by the time a jet of the conductive component-containing liquid from the jet opening reaches the insulating base layer 2.

In such spraying of the conductive component-containing liquid, when the conductive component-containing liquid freely falls as a liquid droplet having a fine diameter, for example, assist gas may be introduced as required.

Examples of the assist gas include nitrogen, argon, and air, and when the nozzle has a diameter of about 1 mmø, the discharge pressure thereof is in the range of, for example, 0.05 to 5.0 kPa, or preferably 0.3 to 1.0 kPa.

When the conductive component-containing liquid is sprayed in a predetermined pattern, for example, a mask may be used as required. More specifically, before spraying of the conductive component-containing liquid, the insulating base layer 2 is covered with a mask having an opening formed in a predetermined pattern. Subsequently, the conductive component-containing liquid is sprayed from above of the insulating base layer 2 and the mask, and the mask is then removed. Thus, the conductive component-containing liquid can be sprayed in the predetermined pattern.

In addition, the conductive component-containing liquid is sprayed, for example, at room temperature.

Thus, the conductive layer 7 can be formed by spraying the conductive component-containing liquid onto the insulating base layer 2.

Conductivity may also be imparted to the conductive layer 7 thus formed by doping (e.g., exposure to iodine) as required.

The conductive layer 7 has a thickness in the range of, for example, 0.01 to 50 μm, preferably 0.1 to 20 μm, or more preferably 0.2 to 10 μm.

Thus, a detection portion 3 can be formed.

In the conductive layer 7 in the detection portion 3 thus formed, an electric path (path) formed of conductive particles between the first electrode 5A and the second electrode 5B causes an electrical disturbance due to the gap formed of non-conductive substance. Such gap of the non-conductive substance provides a predetermined electrical resistance to between the first electrode 5A and the second electrode 5B, and the predetermined electrical resistance varies according to the swelling of the conductive layer 7 based on the absorption and adsorption of a specific gas to be described later.

In the detection portion 3, the type of the conductive layer 7 may be the same or different from each other.

Further, the sensor board 1 is formed as a wired circuit board because it includes the insulating base layer 2 and the conductive pattern 8.

Thereafter, as shown in FIG. 1, a pair of wires 6 is connected to the electrical resistance detector 10. Thus, the sensor board 1 can be produced.

Next, a method for detecting a specific gas using the sensor board 1 will be described.

First, in this method, a sensor board 1 is arranged in a location where a specific gas is desired to be detected.

The specific gas to be detected by the sensor board 1 is not particularly limited, and examples thereof include organic substances such as alkane, alkene, alkyne, allene, alcohol, ether, ketone, aldehyde, carbonyl, and carbanion; and chemical substances such as derivatives of the above-mentioned organic substances (e.g., halogenated derivative, etc.), biochemical molecules such as sugar, isoprene and isoprenoid, fatty acid and derivatives of fatty acid.

Thereafter, in this method, an electrical resistance between a first electrode 5A and a second electrode 5B in a detection portion 3 is detected by an electrical resistance detector 10. More specifically, when a specific gas contacts a non-conductive substance of a conductive layer (conductive material) 7, the non-conductive substance absorbs or adsorbs the specific gas and then swells according to the type and/or the amount (concentration) of the specific gas. This also causes the conductive layer 7 to swell, thereby changing the electrical resistance value between the first electrode 5A and the second electrode 5B in the conductive layer 7. This change in the electrical resistance value is detected by the electrical resistance detector 10.

By analyzing the detected change in the electrical resistance value by a computer, which is not shown, having a given library, the specific gas is qualitatively and/or quantitatively analyzed for the type and/or the amount (concentration) thereof.

These analyses for the change in the electrical resistance value can be performed according to the description of Japanese Unexamined Patent Publication No. 11-503231 or U.S. Pat. No. 5,571,401.

In the sensor board 1, the specific gas can be reliably detected in the detection portion 3 by detecting the electrical resistance value of the conductive layer 7 of which the swelling ratio changes according to the type and the amount of the specific gas, by the electrical resistance detector 10.

Generally, in the formation of the conductive layer 7, when a conductive component-containing liquid is applied to an insulating base layer 2 using a coating method such as solution casting, air spraying, or drop coating, the conductive component-containing liquid thus applied wet-spreads over the insulating base layer 2 until it dries. Therefore, when an organic solvent in the conductive component-containing liquid evaporates, agglomeration and uneven distribution of the conductive particles may occur, resulting in difficulty in uniformly forming the conductive layer 7 having a predetermined thickness.

However, in the method for producing the sensor board 1, since the conductive component-containing liquid is sprayed onto the insulating base layer 2 by an ultrasonic spray method, the organic solvent can be evaporated during the spraying. Thus, wetting and spreading of the conductive component-containing liquid can be suppressed, so that the thickness of the conductive layer 7 can be made uniform.

Further, in the method for producing the sensor board 1, since the conductive component-containing liquid is sprayed by the ultrasonic spray method to form the conductive layer 7, there is little loss of the conductive component-containing liquid, which is highly cost effective.

In the above explanation, the sensor board 1 is exemplified and the specific substance to be detected is described as a gas. The sensor board of the present invention does not limit the state of the substance to be detected, and, for example, the specific substance to be detected may be a liquid.

In the above explanation, one detection portion 3 is provided. However, the number of the detection portion 3 is not particularly limited and, for example, two or more detection portions may be provided, though not shown.

Figure 4:
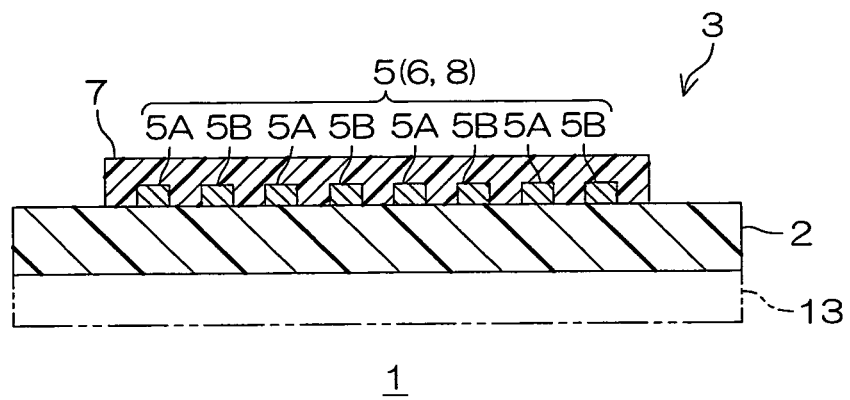
FIG. 4 is a sectional view of a sensor board of another embodiment (embodiment in which eight electrodes are provided in a detection portion) according to the present invention.

In the above explanation, the electrode 5 in the detection portion 3 is formed in the form of a pair of electrodes 5 (the first electrode 5A and the second electrode 5B). However, the number thereof is not particularly limited as long as it is two or more and is an even number so that the electrodes may be connected to the electrical resistance detector 10. For example, as shown in FIG. 4, the electrode 5 may be formed from eight electrodes, that is, four first electrodes 5A and four second electrodes 5B. In FIG. 4, the first electrodes 5A and the second electrodes 5B are alternately arranged in the widthwise direction (in parallel).

Such arrangement of the electrodes 5 can achieve detection of the type and the amount (concentration) of a specific gas with even higher accuracy.

In the above explanation, the undersurface of the insulating base layer 2 is exposed. However, for example, as shown in phantom line in FIG. 3, the undersurface of the insulating base layer 2 can be covered with a metal layer 13.

The metal layer 13 is formed under the insulating base layer 2, and more specifically, is provided over the entire undersurface of the insulating base layer 2.

A metal material that is used to form the metal layer 13 includes, for example, stainless steel, 42-alloy, aluminum, copper-beryllium, and phosphor bronze. Preferably, a stainless steel foil is used from the viewpoint of corrosion resistance.

To provide the metal layer 13, for example, the above-mentioned metal layer 13 is preliminarily prepared and then, the insulating base layer 2 is formed. Alternatively, the metal layer 13 and the insulating base layer 2 may be prepared as a two-layer substrate on which the metal layer 13 and the insulating base layer 2 are preliminarily sequentially laminated. Further alternatively, they may be prepared as a three-layer substrate on which the metal layer 13, the insulating base layer 2, and a conductive layer (a conductive layer for forming a conductive pattern 8) preliminarily sequentially laminated. Commercially available products can be used as the three-layer substrate, and for example, a liquid crystal polymer copper-clad laminate (ESPANEX L series, double-sided, standard type/P type, manufactured by Nippon Steel Chemical Co., Ltd.) in which the insulating base layer 2 made of liquid crystal polymer and the conductive layer made of copper are preliminarily laminated on the surface of the metal layer 13 made of copper is used.

The metal layer 13 has a thickness in the range of, for example, 0.05 to 50 μm, or preferably 0.1 to 20 μm.

When such metal layer 13 is provided under the insulating base layer 2, particularly the insulating base layer 2 made of insulating material having high gas permeability, the metal layer 13 can cut off the gas to be brought into contact with the insulating base layer 2 from the underside, so that the insulating base layer 2 can be prevented from swelling due to absorption of water vapor in the ambient air, and the conductive layer 7 can be prevented from being affected due to penetrating of gas and water vapor from the undersurface of the insulating base layer 2. Therefore, a detection error based on the swelling of the insulating base layer 2 and a detection error based on the insulating base layer 2 affected by the penetration can be prevented.

Figure 5:
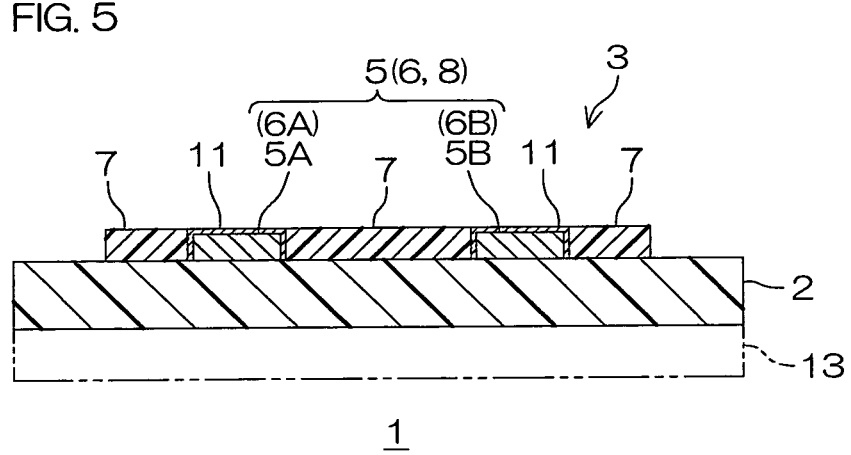
FIG. 5 is a sectional view of a sensor board of another embodiment (embodiment in which a conductive layer covers only each side surface of the electrodes) according to the present invention.

Further, in the above explanation, the conductive layer 7 is formed so as to cover the surfaces of the electrodes 5, that is, the upper surfaces and the side surfaces of the electrodes 5. However, the conductive layer 7 may be formed so as to connect with the first electrode 5A and the second electrode 5B, and, for example, as shown in FIG. 5, the conductive layer 7 can be formed so as to cover only the side surfaces of the electrodes 5 (side surfaces of the protective layer 11). In each detection portion 3, the conductive layer 7 is formed so that its upper surface is flush with the upper surface of the protective layer 11 in the width direction.

In the above explanation, the protective layer 11 is formed so as to cover the conductive pattern 8. However, for example, although not shown, the protective layer 11 can be formed so as to cover only the electrodes 5 but not to cover the wires 6 that are not included in the region of the detection portion 3.

Furthermore, in the above explanation, the protective layer 11 is formed. However, for example, although not shown, the electrodes 5 and the conductive layer 7 can be directly contact with each other without forming the protective layer 11.

EXAMPLES

While in the following, the present invention is described in further detail with reference to Examples and Comparative Examples, the present invention is not limited to any of them.
(Production of Sensor Board)

Example 1

A liquid crystal polymer copper-clad laminate (product number: ESPANEX L-12-25-00NE, single-sided, standard type, manufactured by Nippon Steel Chemical Co., Ltd.) in which a 12 µm thick copper foil as a conductive layer was preliminarily laminated on a surface of a 25 µm thick liquid crystal polymer sheet as an insulating base layer was prepared, and a conductive pattern having a pair of electrodes was formed by a subtractive method (cf. FIG 3(b)). Each of the electrodes (wires) has a width of 0.25 mm and a spacing between the wires (electrodes) was 1.5 mm.

Then, a 0.5 µm thick gold layer was formed on surfaces of the conductive patterns (cf. FIG. 3(c)).

Subsequently, 40 mg of carbon black (Black pearl 2000), 150 mg of polyvinyl alcohol, and 20 mL of toluene were blended and mixed to prepare a conductive component-containing liquid. The conductive component-containing liquid thus prepared has a viscosity at 25° C. of 0.01 Pa·s.

The conductive component-containing liquid thus obtained was then sprayed onto the insulating base layer 2 using an ultrasonic spray nozzle (AccuMist Nozzle, manufactured by Sono-Tek Corporation) (cf. FIG. 3(d)).

To spray the conductive component-containing liquid, the frequency of the ultrasonic wave was set to 60 kHz, and an assist gas (air gas, a discharge pressure of 0.4 kPa, and a nozzle diameter of about 1 mmø) was introduced at 25° C. The distance from the distal end of the ultrasonic spray nozzle to the insulating base layer was 4 cm.

Example 2

The sensor board was produced in the same manner as in Example 1 except that the frequency of the ultrasonic wave was set to 120 kHz.

Comparative Example 1

The sensor board was produced in the same manner as in Example 1 except that the conductive component-containing liquid was sprayed onto the insulating base layer 2 using an airbrush (HP-CPlus) manufactured by Anest Iwata Corporation.

Comparative Example 2

The sensor board was produced in the same manner as in Example 1 except that the conductive component-containing liquid was added dropwise onto the insulating base layer 2 using a known syringe.
(Evaluation)
(Appearance)

In the sensor board produced in each of Examples 1 and 2, a conductive layer was formed uniformly on the surface of the sensor board.

In the sensor board produced in Comparative Example 1, agglomeration of carbon black was confirmed on the surface of the sensor board.

In the sensor board produced in Comparative Example 2, the entire surface of the sensor board got wet with the organic solvent, so that agglomeration and uneven distribution of carbon black were confirmed.
(Continuity Between Electrodes)

In the sensor board produced in each of Examples 1 and 2, a stable resistance value was able to be obtained.

In the sensor board produced in Comparative Example 1, although there was continuity between the electrodes, a stable resistance value was not able to be obtained.

In the sensor board produced in Comparative Example 2, there was little continuity between the electrodes.
(Sensor Function)

The sensor board produced in each of Examples 1 and 2 was exposed to a gas (vapor) atmosphere containing ethanol gas at a known concentration and the ethanol gas in the atmosphere was detected.

As a result, the ethanol gas at the known concentration was able to be detected by the sensor board of Examples 1 and 2.

While the illustrative embodiments of the present invention are provided in the above description, such is for illustrative purpose only and it is not to be construed limitative. Modification and variation of the present invention that will be obvious to those skilled in the art is to be covered by the following claims.

What is claimed is:

1. A method for producing a sensor board comprising the steps of preparing an insulating layer; forming at least a pair of electrodes on the insulating layer; and forming a conductive layer by spraying a conductive component-containing liquid onto the insulating layer by an ultrasonic spray method so as to cover the electrodes
wherein the conductive component-containing liquid contains an organic solvent, and
wherein the organic solvent in the conductive component-containing liquid evaporates by the time liquid droplets of the conductive component-containing liquid reaches the insulating layer during the ultrasonic spray method so that the conductive layer has a uniform thickness.

2. The method for producing a sensor board according to claim 1, wherein the conductive component-containing liquid contains a conductive particle, and a non-conductive substance.

3. The method for producing a sensor board according to claim 1, wherein the conductive component-containing liquid has a viscosity at 25° C. of 0.05 Pa·s or less.

4. The method for producing a sensor board according to claim 1, wherein the frequency of an ultrasonic wave of the ultrasonic spray method is in the range of 60 to 150 kHz.

5. The method for producing a sensor board according to claim 1, wherein in the ultrasonic spray method, with an ultrasonic spray device installed above and 30 mm to 200 mm spaced apart from the insulating layer so as to face the insulating layer, the conductive component-containing liquid is sprayed from a jet opening of the ultrasonic spray device onto the insulating layer.

* * * * *